United States Patent [19]

Swenson

[11] Patent Number: Plant 5,771

[45] Date of Patent: Jul. 22, 1986

[54] GRAPEVINE-ST. PEPIN

[75] Inventor: Elmer Swenson, Osceola, Wis.

[73] Assignee: Swenson-Smith Vines, Inc., Excelsior, Minn.

[21] Appl. No.: 663,420

[22] Filed: Oct. 22, 1984

[51] Int. Cl.[4] ..... A01H 5/03

[52] U.S. Cl. ..... Plt./47

[58] Field of Search ..... Plt./47

*Primary Examiner*—Robert E. Bagwill

*Attorney, Agent, or Firm*—Merchant, Gould, Smith, Edell, Welter & Schmidt

[57] ABSTRACT

A grapevine which exhibits winter hardiness down to −32° Fahrenheit in central Wisconsin and Minnesota, with usefulness as a white wine grape, having desirable aroma, flavor, acidity and sugar content, and with no foxiness or labrusca flavor or aroma.

2 Drawing Figures

ORIGIN AND REPRODUCTION

The present invention relates to a new and distinct variety of grapevine which has been produced by me as a result of an ongoing grape breeding program at my vineyard and nursery located in Polk County, near Osceola, in northern Wisconsin. This variety has also been secondarily tested at sites located in central and southern Minnesota. The present variety is characterized by good winter hardiness and usefulness as a wine grape, having desirable aroma, flavor, acidity and sugar content, with no foxiness or labrusca flavor or aroma.

For some 40 years, I have been growing a large number of grapevines at my above-noted nursery and vineyard in northern Wisconsin with a breeding program directed to the production of grapevines having the desirable winter hardiness for northern states and commercially useful as wine and/or table grapes.

By way of background, it is noted that there have been very few desirable commercial grape varieties for growing in the harsh northern climate of Minnesota, Wisconsin and similar northern states. While this northern region has a summer thermal accumulation similar to that of the best grape growing areas of the world, the low winter temperatures have generally prevented development of vineyards in this region because of the lack of suitably hardy grape varieties.

Current vineyard cultural practices in the noted northern region generally involve early fall pruning, after which the vines are removed from trellises and laid upon the ground and covered for wintering. In the spring, the vines are uncovered and re-trellised, all of which involves increased labor costs, which are generally prohibitive and make it quite difficult for northern vineyards in such climates to operate profitably. Accordingly, for grapevines to be of high commercial value to vineyards in such northern regions, such as Minnesota and Wisconsin, it has become nearly essential that the varieties be hardy enough to remain on the trellises throughout the winter months without removal and winter covering. The present variety has this desirable characteristic for the southern portion and up to the central portion of the northern tier of states.

This new variety of grapevine was selected by me for its combination of good winter hardiness and usefulness as a wine grape, producing a white wine similar to the Seyval which is one of its parents.

The present variety is a result of my above-noted breeding program, in which my varietal selections are designated by number with the prefix ES. This variety is a select seedling resulting from my cross of ES114 (Minnesota 78×Seibel 1000) ×Seyval. While under test, I have identified the present variety as ES282 and selected the name "St. Pepin" therefor.

I have reproduced the present variety by means of cuttings and have carefully observed the variety for several years. The continual observation and testing of the present variety has convinced me that it is a new and improved cultivar of grapevine, as indicated by the following unique combination of outstanding qualities which distinguish this variety from all other varieties of grapevine known to me.

SUMMARY OF CHARACTERISTICS

The unique combination of characteristics of the present variety ES282, named "St. Pepin", are as follows:

1. Winter Hardiness. The present variety has excellent winter hardiness for zones such as southernmost Minnesota and Wisconsin, whereby the vines may remain on the trellises throughout the winter without covering. More specifically, this variety has survived on trellises with a winter temperature of −32° Fahrenheit with no apparent injury to its vines and approximately 50% bud injury with no winter covering. Such survival has been at my vineyard located near Osceola, Wis., in central Wisconsin, and at a secondary test site located near Excelsior, Minn., which is in central Minnesota. My observations indicate this variety to be several degrees more winter hardy than the Seyval variety which is its pollen parent.

2. Low Acidity. The present variety has also produced grapes of relatively low acidity for a cold climate grape, a desirable attribute for wine grapes. In years of relatively poor growing conditions, this vine's acidity has averaged 0.96% and in years of good growing conditions its acidity has averaged 0.85%.

3. Sugar Content. This cultivar has an average sugar content of 17.6% in the most northern test site, and in its most southern site near Excelsior, Minn. it averages a brix or sugar content of 21.0%.

4. Flavor and Color. A so-called foxiness or labrusca flavor and aroma is an objectionable characteristic generally for wine grapes, yet is typical of previous varieties having good winter hardiness. The usual foxiness or labrusca flavor or aroma is not apparent in this variety.

The variety produces a white wine that compares favorably with many German style white wines.

ASEXUAL REPRODUCTION

The present variety has been asexually reproduced by me by means of vine cuttings at my nursery and vineyard in Polk County, near Osceola, Wis. Such asexual reproduction confirms that the characteristics and qualities stated herein for this variety are true to form and consistent through succeeding propagations.

DETAILED DESCRIPTION

The accompanying drawings comprise photographs showing characteristics of this new variety. The photographs were taken of specimens of the variety growing at a test site in central Minnesota. The color photographs depict color features as true as reasonably possible.

The following is a detailed description or specification of the pomological characteristics of this new variety, with color terminology or references in accordance with The Royal Horticulture Society Colour Chart. Where dimensions, sizes, colors, and other characteristics are given, it is to be understood that the same are approximations of averages as they appear under conditions prevailing at secondary test sites as well as my vineyard near Osceola, Wis.

Vine:

*Growth habit.*—Very upright and perhaps as pronounced as the typical Vinifera grapevine. Tends to form a somewhat open canopy. Medium vigor.

*Trunk.*—Thick and sheds bark in long strips but trunk needs support. Inner bark color is closest to Greyed Orange Color Group 165C.

*Canes.*—Average length is 1.8 meters. Spacing between nodes averages 9.4 centimeters. Tendrils are intermittent, and usually skip every third node.

Figure 1:
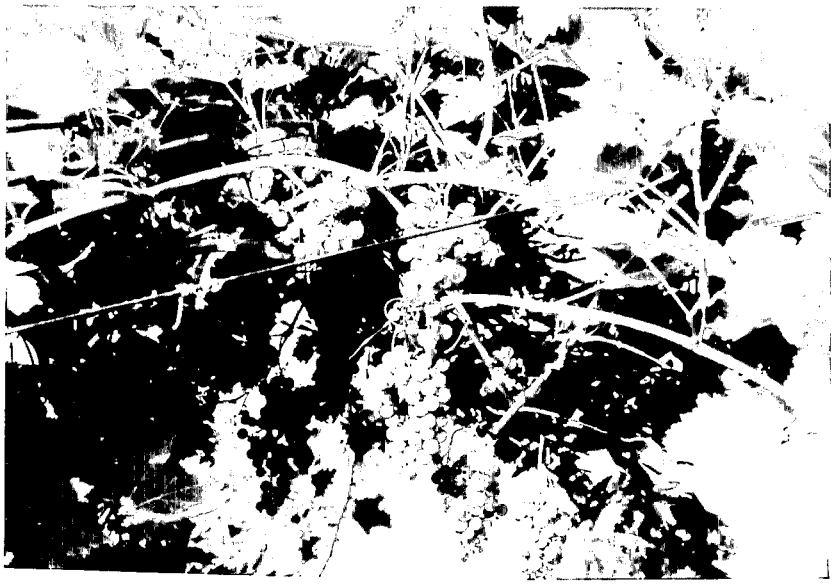
FIG. 1 is a color photograph showing the form and growth of a mature vine of the present variety, and also showing typical fruit clusters.
Figure 2:
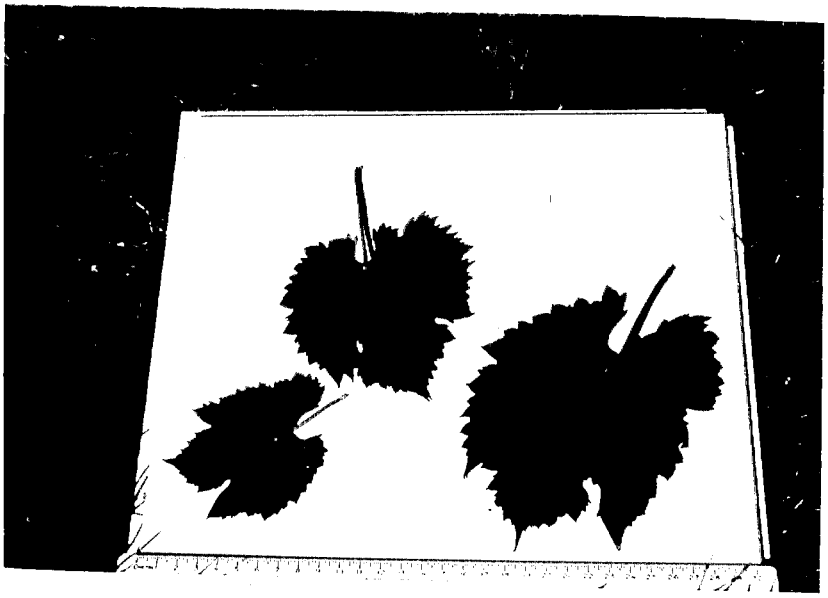
FIG. 2 is a color photograph showing the mature summer leaf form for typical leaves of the variety.

Foliage:

*Leaves.*—Top sinuses about 1 centimeter deep and no other sinuses apparent with the petiole sinus described as U-shaped. Serrate margins can best be described by photograph in FIG. 1. Top mature leaf color is Yellow Green Group 147A; leaf underside is closest to Color Group 138A; petiole is Yellow Green Group 144C. The average mature leaf is approximately 10 centimeters wide by 10 centimeters long.

Grapes:

*Maturity.*—Early mid-season. Mid-September to late September at Excelsior, Minn. Often ripens about the same time as the Seyval grape.

*Size of berry.*—Natural 1.1 centimeter average.

*Shape of berry.*—Spherical.

*Ripening.*—Ripens evenly. Fruit holds well on the vine with no shattering.

*Color of berry.*—Closest to Yellow Green Group 146B.

*Cluster.*—Medium packed; definitely not tightly packed. General cluster shape would be slightly cone-shaped. Medium clusters which measure: 2.5 centimeter stem; 10 centimeter cluster width; 12 centimeters in length. Average cluster weight is approximately 6 ounces with 60 to 80 berries per cluster.

*Seeds.*—2 to 4 seeds per berry. Seed color: reddish brown.

*Pulp.*—Juicy. Pulp color closest to Yellow Green 150D.

*Juice color.*—Free run juice is close to Green White 157B to 157C.

*Sugar and acid.*—21.0° brix and 0.89 acid, as tested on Sept. 21, 1983, at Excelsior, Minn., vine site.

*Clusters per shoot.*—Usually three.

*Other characteristics.*—Good resistance to downy mildew and black rot at sites tested. Imperfect flowers, and not self pollinating under test, but has never failed to set berries when planted near perfect flowering vines such as "LaCrosse". The fruit has superior fruitiness, freshness and blending qualities which make it well worth the winter protection procedure where winter temperatures may exceed −32° F. Based upon current testing, this "St. Pepin" variety will enable one to produce a superior white varietal or blended wine from grapes grown in the northern tier of states.

I claim:

1. A new and distinct variety of grapevine, substantially as shown and described herein, characterized particularly as to novelty by the unique combination of winter hardiness down to −32° Fahrenheit in central Wisconsin and Minnesota, with grapes of relatively low acidity, high sugar content, a desirable aroma and flavor with an absence of foxiness or labrusca and producing a good quality white wine, as well as being highly desirable in view of its blending qualities.

* * * * *